US011547562B2

(12) United States Patent
Krivoruchko

(10) Patent No.: US 11,547,562 B2
(45) Date of Patent: Jan. 10, 2023

(54) BALLOON CATHETER INCLUDING BRAIDED PORTIONS FORMING PERFUSION OPENINGS

(71) Applicant: Medtronic Vascular, Inc., Santa Rosa, CA (US)

(72) Inventor: Michael Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 263 days.

(21) Appl. No.: 17/098,416

(22) Filed: Nov. 15, 2020

(65) Prior Publication Data

US 2021/0068952 A1    Mar. 11, 2021

Related U.S. Application Data

(63) Continuation of application No. 15/465,830, filed on Mar. 22, 2017, now Pat. No. 10,849,745.

(Continued)

(51) Int. Cl.
*A61F 2/24* (2006.01)
*A61M 25/00* (2006.01)
*A61M 25/10* (2013.01)

(52) U.S. Cl.
CPC ......... *A61F 2/2433* (2013.01); *A61M 25/005* (2013.01); *A61M 25/0045* (2013.01);
(Continued)

(58) Field of Classification Search
CPC ....... A61F 2/2433; A61F 2/958; A61M 25/10; A61M 25/005; A61M 25/0045; A61M 2025/1095; A61M 2025/1093
See application file for complete search history.

(56) References Cited

U.S. PATENT DOCUMENTS 6,193,685 B1   2/2001  Goodin
7,618,432 B2  11/2009  Pedersen et al.
(Continued)

FOREIGN PATENT DOCUMENTS

EP    1561487 A2   8/2005
WO    0135858 A1   5/2001

OTHER PUBLICATIONS https://www.labce.com/spg28714_size_and_appearance_of_cellular_elements.aspx; (2019 by LabCE).
(Continued)

*Primary Examiner* — Majid Jamialahmadi
(74) *Attorney, Agent, or Firm* — Medler Ferro Woodhouse & Mills PLLC

(57) ABSTRACT

A balloon catheter includes a balloon coupled to a shaft. The shaft includes a proximal perfusion portion disposed proximal of the balloon and a distal perfusion portion disposed distal of the balloon. The proximal and distal perfusion portions each are formed by a respective plurality of wire members woven together to form a respective proximal and distal braided shafts. The plurality of wire members are woven together such that a plurality of perfusion openings are formed between the wire members. The plurality of perfusion openings extend from an outer surface of the respective proximal or distal braided shaft to a lumen of the respective proximal or distal braided shaft. A perfusion lumen extends between the proximal perfusion portion and the distal perfusion portion.

16 Claims, 6 Drawing Sheets

Related U.S. Application Data

(60) Provisional application No. 62/398,541, filed on Sep. 23, 2016.

(52) U.S. Cl.
CPC .... *A61M 25/0052* (2013.01); *A61M 25/0068* (2013.01); *A61M 25/10* (2013.01); *A61M 25/0074* (2013.01); *A61M 2025/1093* (2013.01); *A61M 2025/1095* (2013.01)

(56) References Cited

U.S. PATENT DOCUMENTS

| | | |
|---|---|---|
| 8,486,014 B2 | 7/2013 | Kelly et al. |
| 2006/0074396 A1 | 4/2006 | Stiger |
| 2006/0259137 A1 | 11/2006 | Artof et al. |
| 2007/0106363 A1 | 5/2007 | Weber |
| 2007/0293942 A1 | 12/2007 | Mirzaee |
| 2011/0224628 A1 | 9/2011 | Bodenlenz et al. |
| 2012/0226303 A1 | 9/2012 | Roche et al. |
| 2013/0184742 A1* | 7/2013 | Ganesan ............... A61M 25/10 606/200 |
| 2015/0272732 A1 | 10/2015 | Tilson et al. |
| 2016/0193001 A1 | 7/2016 | Lee et al. |

OTHER PUBLICATIONS

PCT/US2017/023625, The International Search Report and the Written Opinion of the International Searching Authority, dated Jun. 16, 2017.

* cited by examiner

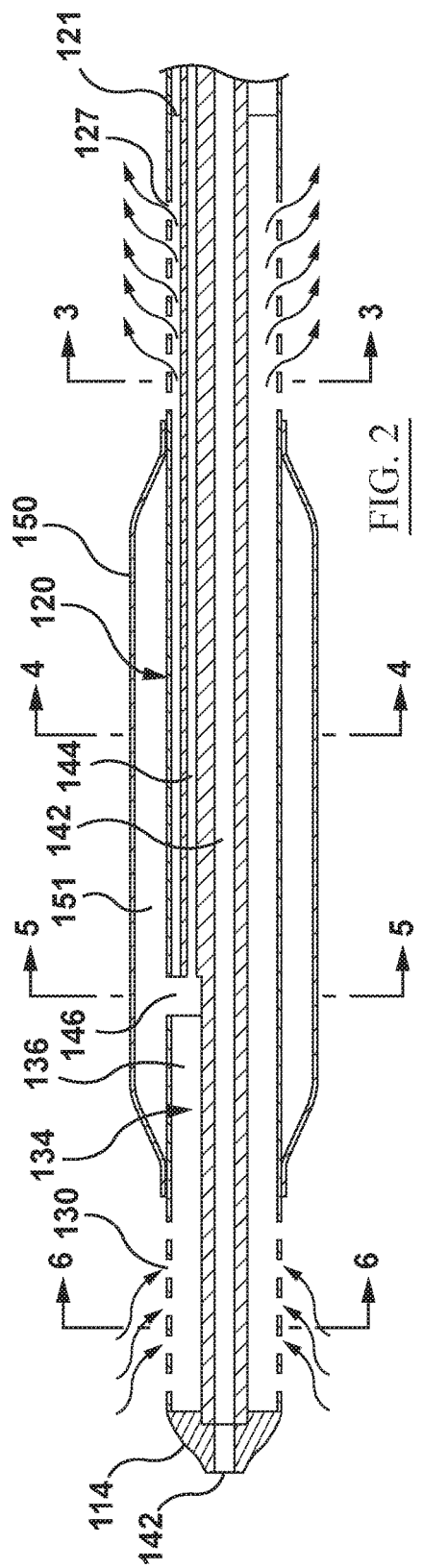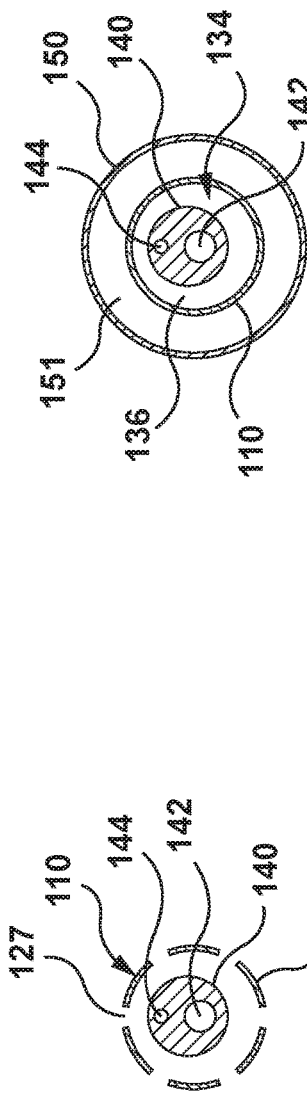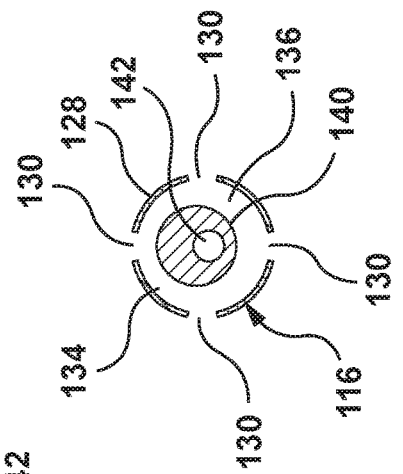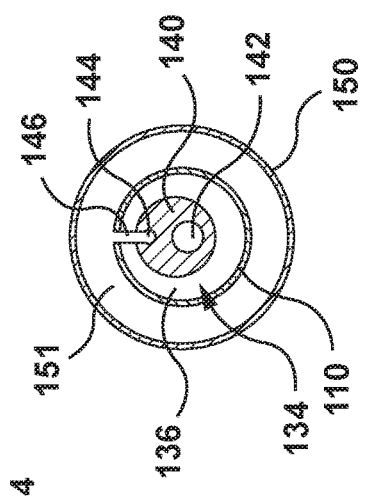
FIG. 2
FIG. 3
FIG. 4
FIG. 5
FIG. 6 ns. Balloon

BALLOON CATHETER INCLUDING BRAIDED PORTIONS FORMING PERFUSION OPENINGS

CROSS-REFERENCE TO RELATED APPLICATIONS

This application is a continuation of U.S. patent application Ser. No. 15/465,830, filed Mar. 22, 2017, which claims the benefit under 35 U.S.C. § 119(e) of the filing date of U.S. Provisional Application No. 62/398,541 filed Sep. 23, 2016, the contents of each of which are incorporated by reference herein in their entirety.

FIELD OF THE INVENTION

The present invention relates to a balloon catheter for deploying a prosthetic heart valve. More particularly, the present invention relates to a balloon catheter with braided portions forming perfusion openings such that a prosthetic heart valve may be deployed without rapid pacing.

BACKGROUND

Heart valves are sometimes damaged by disease or by aging, resulting in problems with the proper functioning of the valve. Heart valve replacement via surgical procedure is often used for patients suffering from valve dysfunctions. Traditional open surgery inflicts significant patient trauma and discomfort, requires extensive recuperation times, and may result in life-threatening complications.

To address these concerns, efforts have been made to perform cardiac valve replacements using minimally invasive techniques. In these methods, laparoscopic instruments are employed to make small openings through the patient's ribs to provide access to the heart. While considerable effort has been devoted to such techniques, widespread acceptance has been limited by the clinician's ability to access only certain regions of the heart using laparoscopic instruments.

Still other efforts have been focused upon percutaneous transcatheter (or transluminal) delivery of replacement cardiac valves to solve the problems presented by traditional open surgery and minimally invasive surgical methods. In such methods, a heart valve prosthesis is radially compressed for delivery via a delivery device, also known as a delivery catheter, and then advanced through a lumen in the native vasculature to the heart, where the heart valve prosthesis is then deployed at the location of the native valve complex.

Various types and configurations of heart valve prostheses are available for percutaneous valve replacement procedures. In general, heart valve prosthetic designs attempt to replicate the function of the valve being replaced and thus will include valve leaflet-like structures. Heart valve prostheses are generally formed by attaching a bioprosthetic valve to a frame made of a wire or a network of wires. Such heart valve prostheses can be contracted radially to introduce the heart valve prosthesis into the body of the patient percutaneously through a delivery catheter. The heart valve prosthesis can be deployed by radially expanding it once positioned at the desired target site.

Some heart valve prostheses are balloon expandable. Balloon expandable prostheses provide some advantages and disadvantages as compared to self-expanding prostheses. One disadvantage is that when using a balloon catheter to radially expand the heart valve prosthesis, the inflated balloon blocks flow through the native valve. Due to the high volume and pressure of blood crossing the native valve, such as the native aortic valve, the balloon may be moved out of place. For example, the balloon may become misshapen and result in unwanted movement proximally or distally (also known as watermelon seeding). Such movement or change in shape of the balloon makes it difficult to accurately locate the heart valve prosthesis, which is mounted on the balloon. In other words, radially expanding the heart valve prosthesis at the proper location within the native heart valve complex is critical to proper functioning of the heart valve prosthesis. When the balloon of a balloon catheter is inflated, it blocks blood flow, which may cause the balloon to shift, thereby deploying the heart valve prosthesis at an improper location. Balloon catheters may also be used in valvuloplasty procedures to open a narrowed heart valve. Valvuloplasty procedures may be performed alone or prior to delivery of a heart valve prosthesis. Balloon catheters used in valvuloplasty procedures also may face high pressures described above, and therefore may become misshapen.

In order to combat the above-described pressure against the inflated balloon, the patient's heart may be placed into "rapid pacing" or "rapid ventricle pacing." In rapid pacing, the patient's heart is stimulated such that the heart beats very rapidly, sometimes described as fluttering or twitching. Due to the rapid pacing, blood does not have sufficient time to fill the chamber of the heart adjacent the valve, such as the left ventricle adjacent the aortic valve. Therefore, without a significant quantity of blood being ejected from the chamber, pressure does not build up against the inflated balloon.

However, rapid pacing may be harmful to some patients. Also, rapid pacing requires a temporary pacer to stimulate the patient's heart. The use of such a temporary pacer increases the cost and time of the procedure. It increases time because the temporary pacer must be temporarily implanted and then removed from the patient. It increases cost by requiring the use of this additional device and by increasing the time of the procedure.

Accordingly, there exists a need for a balloon catheter for prosthetic heart valve deployment that does not require rapid pacing and alleviates the pressure build-up such that a balloon-expandable heart valve prosthesis may by accurately implanted.

SUMMARY OF THE INVENTION

Embodiments hereof relate to a balloon catheter for delivery and deployment of a heart valve prosthesis and/or for use in valvuloplasty procedures. The balloon catheter includes a balloon coupled to a shaft. The shaft includes a proximal perfusion portion disposed proximal of the balloon and a distal perfusion portion disposed distal of the balloon. The proximal and distal perfusion portions each are formed by a respective plurality of wire members woven together to form a respective proximal and distal braided shaft. The plurality of wire members are woven together such that a plurality of perfusion openings are formed between the wire members. The plurality of perfusion openings extend from an outer surface of the respective proximal or distal braided shaft to a lumen of the respective proximal or distal braided shaft. A perfusion lumen extends between the proximal perfusion portion and the distal perfusion portion.

Embodiments hereof also relate to a system including a balloon catheter with a heart valve prosthesis mounted thereon. The balloon catheter includes a balloon coupled to a shaft. The shaft includes a proximal perfusion portion disposed proximal of the balloon and a distal perfusion portion disposed distal of the balloon. The proximal and distal perfusion portions each are formed by a respective plurality of wire members woven together to form a respective proximal and distal braided shaft. The plurality of wire members are woven together such that a plurality of perfusion openings are formed between the wire members. The plurality of perfusion openings extend from an outer surface of the respective proximal or distal braided shaft to a lumen of the respective proximal or distal braided shaft. A perfusion lumen extends between the proximal perfusion portion and the distal perfusion portion. The heart valve prosthesis is mounted on the balloon in a radially compressed configuration for delivery to the site of a native heart valve. The balloon is configured to be inflated at the site to radially expand the heart valve prosthesis from the radially compressed configuration to a radially expanded configuration.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2 is a longitudinal cross-sectional view of a distal portion the balloon catheter of FIG. 1.

FIG. 3 is a cross-sectional view taken along line 3-3 of FIG. 2.

FIG. 4 a cross-sectional view taken along line 4-4 of FIG. 2.

FIG. 5 a cross-sectional view taken along line 5-5 of FIG. 2.

FIG. 6 a cross-sectional view taken along line 6-6 of FIG. 2.

DETAILED DESCRIPTION

Specific embodiments of the present invention are now described with reference to the figures, wherein like reference numbers indicate identical or functionally similar elements. The terms "distal" and "proximal", when used in the following description to refer to a guidewire, catheter, and/or other system component hereof are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal", when used in the following description to refer to a native vessel or native valve are used with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the invention or the application and uses of the invention. Furthermore, there is no intention to be bound by any expressed or implied theory presented in the preceding technical field, background, brief summary, or the following detailed description.

Figure 1:
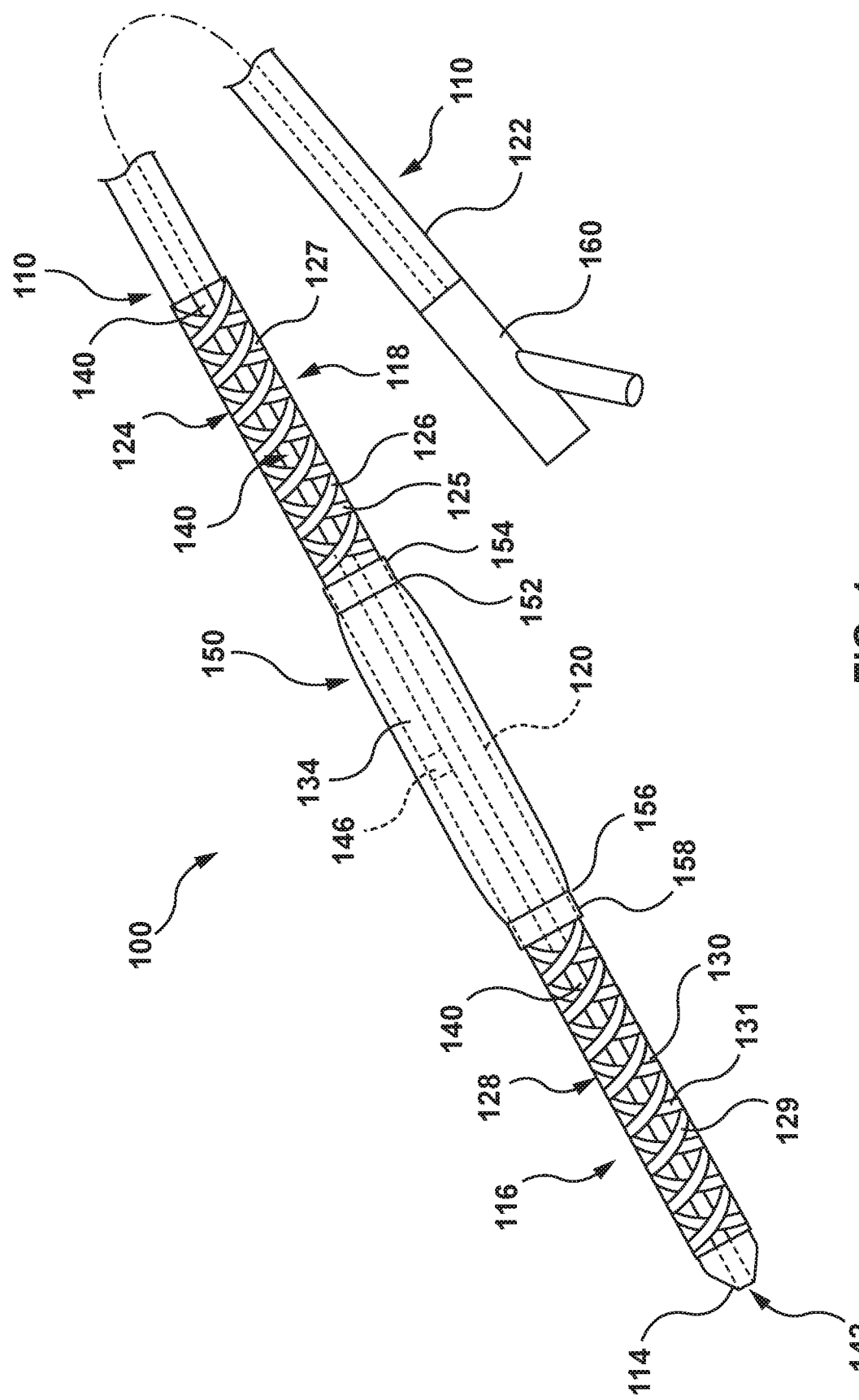
FIG. 1 is a side view illustration of a balloon catheter in accordance with an embodiment hereof.

FIGS. 1-7A illustrate a balloon catheter 100 in accordance with an embodiment hereof. The balloon catheter 100, as shown in FIG. 1, includes an outer shaft 110, an inner shaft 140, a distal tip 114, and a balloon 150. A luer or hub 160 may be attached to a proximal end of the balloon catheter 100. The balloon catheter 100 may be used in a valvuloplasty procedure or may be configured to deliver and deploy a balloon-expandable heart valve prosthesis, as described in further detail below.

In an embodiment, the outer shaft 110 includes a distal perfusion portion 116, a balloon portion 120, a proximal perfusion portion 118, and a proximal portion 122. The outer shaft 110 defines a lumen 134 therein. In an embodiment, the distal perfusion portion 116 extends proximally from the distal tip 114, the balloon portion 120 extends proximally from the distal perfusion portion 116 and within the balloon 150, the proximal perfusion portion 118 extends proximally from the balloon portion 120, and the proximal portion 122 extends proximally from the proximal perfusion portion 118, as shown in FIG. 1. However, other portions or sections may be included. For example, a non-perfusion portion may be disposed between the distal perfusion portion 116 and the distal tip 114. Other variations may also be made or other portions added. For the purposes of this disclosure, it is desirable for the distal perfusion portion 116 to be distal to the balloon 150, the proximal perfusion portion 118 to be proximal of the balloon 150, and a lumen or other way to transfer blood flow between the distal perfusion portion 116 and the proximal perfusion portion 118 be provided.

The proximal portion 122 and the balloon portion 120 of the outer shaft 110 may be made from a polymeric material, non-exhaustive examples of which include polyethylene, polyether block amide (PEBA), polyamide and/or combinations thereof, either blended or co-extruded. Optionally, the proximal portion 122 and the balloon portion 120 of the outer shaft 110 may be formed as a composite having a reinforcement material incorporated within a polymeric body in order to enhance strength and/or flexibility. Suitable reinforcement layers include braiding, wire mesh layers, embedded axial wires, embedded helical or circumferential wires, and the like.

Figure 7:
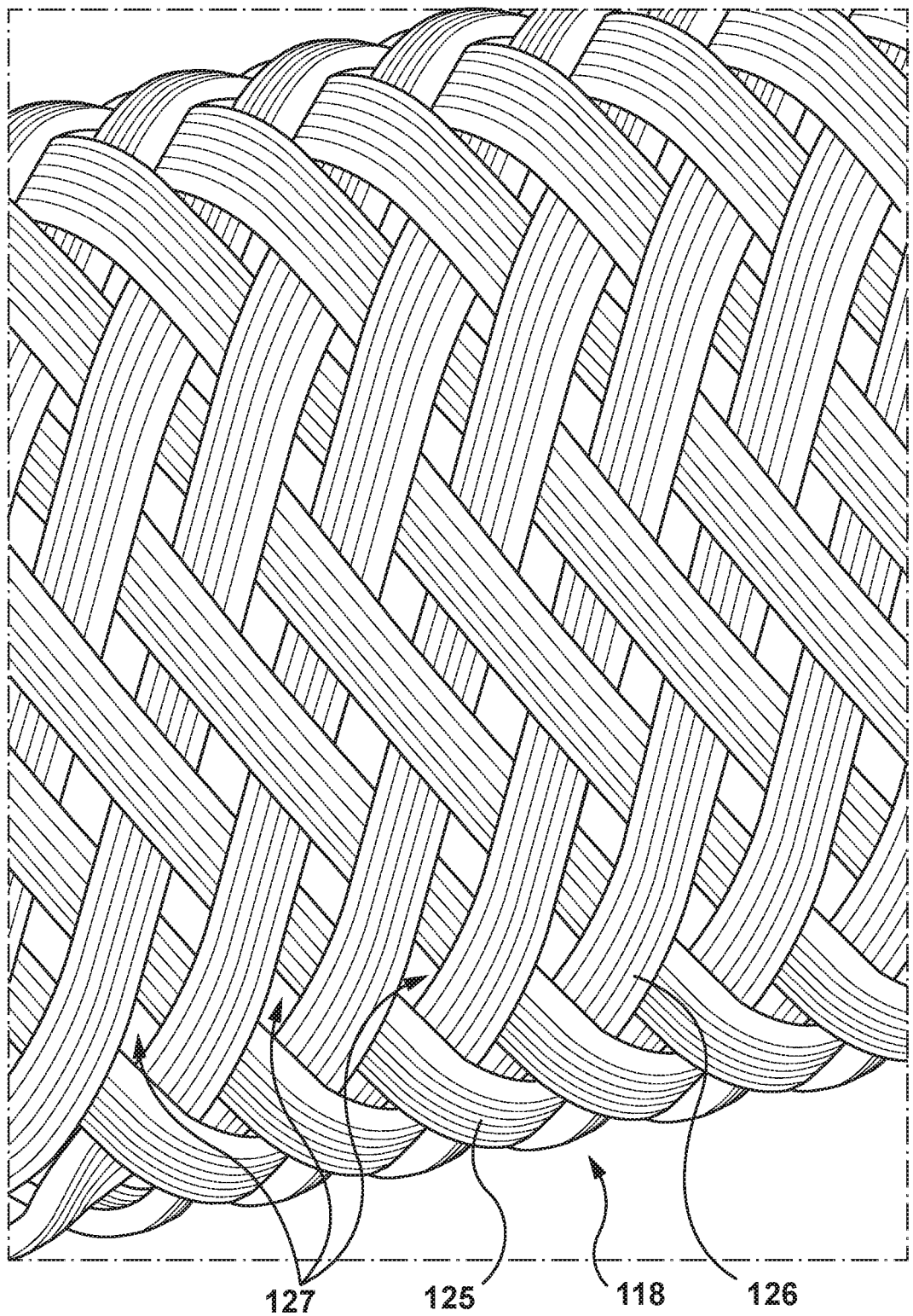
FIG. 7 is a close-up view of an embodiment of a portion of the proximal perfusion portion of the balloon catheter of FIG. 1.
Figure 7A:
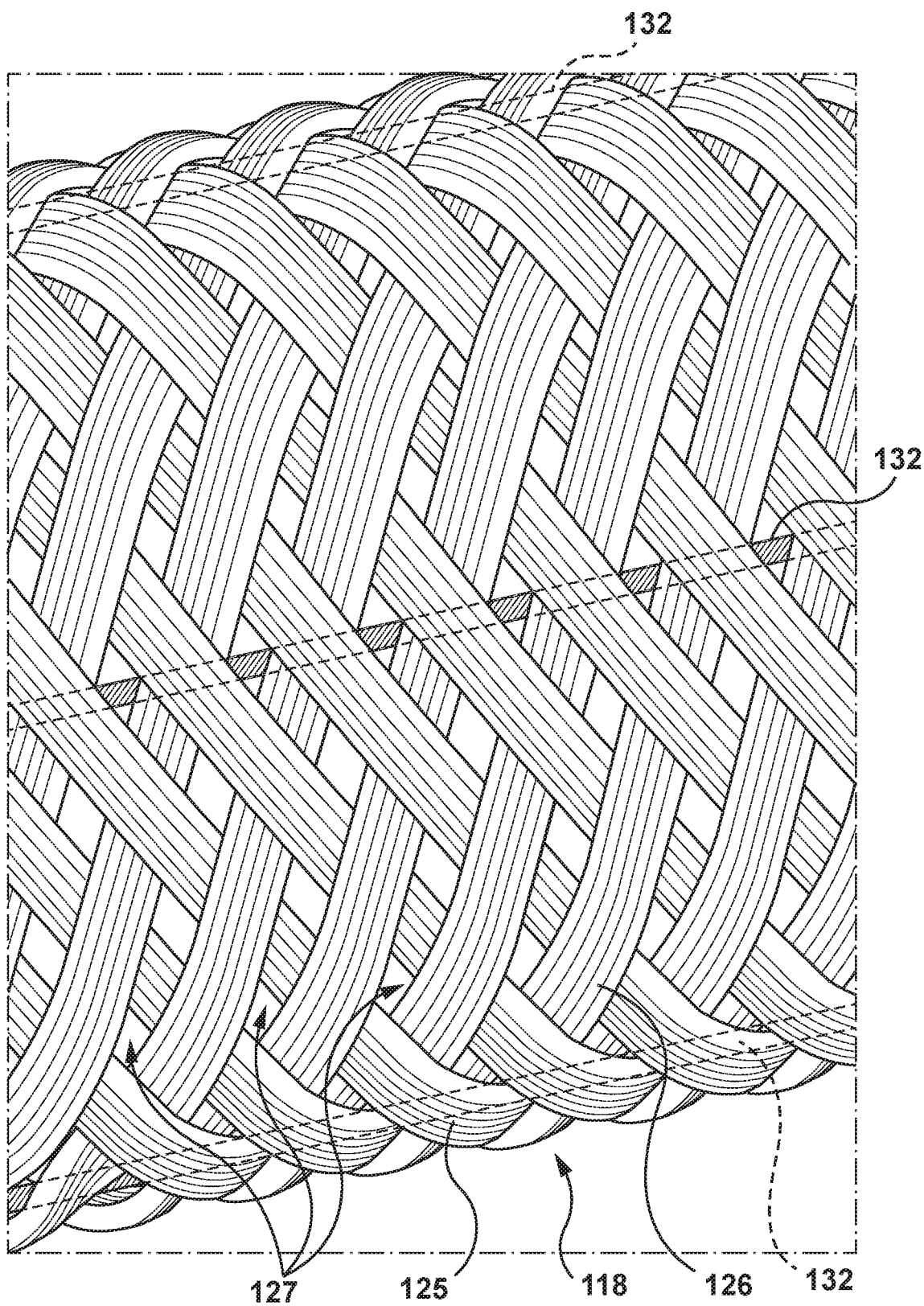
FIG. 7A is a close-up view of another embodiment of a portion of the proximal perfusion portion of the balloon catheter of FIG. 1.

The proximal perfusion portion 118, as shown in FIG. 1 and FIGS. 7-7A, includes a proximal braided shaft 124. The proximal braided shaft 124 includes a plurality of wire members 125, 126 woven to form a generally tubular shape, as shown in FIGS. 1 and 7-7A. The proximal braided shaft 124 is configured to provide flexibility, strength, and rigidity to the proximal perfusion portion 118. Moreover, the proximal braided shaft 124 forms a plurality of proximal perfusion openings 127 between the adjacent woven wire members 125, 126. The proximal perfusion openings 127 extend from an outer surface of the proximal braided shaft 124 to the lumen 134 of the outer shaft 110. The weave of the proximal braided shaft 124 should be loose enough to provide sufficiently large proximal perfusion openings 127 to provide sufficient blood flow in or out of the proximal perfusion portion 118, as described in more detail below, but also tight enough to maintain structural integrity of the outer shaft 110 at the proximal perfusion portion 118. In an embodiment, the proximal perfusion openings 127 are sized approximately 0.1 mm-5 mm in width. However, other sizes may be utilized if suitable for the purposes described herein. The proximal braided shaft 124 is formed by weaving together the plurality of wire members 125, 126 in opposite directions in a one-over-one pattern. The weaving pattern, number and size of the wire members 125, 126 may be varied. The wire members 125, 126 of the proximal braided shaft 124 may be formed from materials such as, but not limited to, stainless steel, Nitinol, or other materials suitable for the purposes described herein. The wire members 125, 126 may also be coated prior to weaving, if desired. For example, and not by way of limitation, the wire members 125, 126 may be coated with a polymer material prior to weaving.

In an embodiment shown in FIG. 7A, longitudinal stiffening wires 132 are attached to the proximal braided shaft 124 along an inner surface of the proximal braided shaft 124. The stiffening wires 132 may be provided if, in order to provide sufficiently sized proximal perfusion openings 127, the weave of the proximal braided shaft 124 needs to be so loose as to not provide sufficient structural support. In particular, the proximal braided shaft 124 must still provide sufficient pushability to allow the balloon catheter 100 to be advanced to the treatment site. Adding stiffening wires 132 increases pushability without significantly reducing the overall size of the proximal perfusion openings 127. In FIG. 7A, the stiffening wires 132 are shown approximately 90 degrees apart from each other around the circumference of the inner surface of the proximal braided shaft 124, thereby resulting in four stiffening wires 132 (only three showing). However, more or fewer stiffening wires 132 may be utilized. The stiffening wires 132 may be limited to the proximal braided shaft 124 or may extend into other portions of the outer shaft 110. For example, and not by way of limitation, the stiffening wires 132 may extend from a proximal end of the proximal portion 122 to a distal end of the distal perfusion portion 116. In other embodiments, the stiffening wires 132 may stop proximally of the distal perfusion portion 116 such that the distal perfusion portion 116 may be more flexible than portions proximal thereof. In other embodiments, the number of stiffening wires 132 may be reduced moving distally along the outer shaft 110 such that the outer shaft 110 becomes more flexible towards the distal end of the outer shaft 110. The stiffening wires 132 may be made of any material to improve longitudinal pushability, such as, but not limited to, stainless steel, metal alloys, and other materials.

The distal perfusion portion 116, as shown in FIG. 1, includes a distal braided shaft 128. The distal braided shaft 128 includes a plurality of wire members 129, 131 woven to form a generally tubular shape, as shown in FIG. 1. The distal braided shaft 128 is configured to provide flexibility, strength, and rigidity to the distal perfusion portion 116. Moreover, the distal braided shaft 128 forms a plurality of distal perfusion openings 130 between the adjacent woven wire members 129, 131. The distal perfusion openings 130 extend from an outer surface of the distal braided shaft 128 to the lumen 134 of the outer shaft 110. The weave of the distal braided shaft 128 should be loose enough to provide sufficiently large distal perfusion openings 130 to provide sufficient blood flow into or out of the distal perfusion portion 116, as described in more detail below, but also tight enough to maintain structural integrity of the outer shaft 110 at the distal perfusion portion 116. In an embodiment, the distal perfusion openings 130 are sized approximately 0.1 mm-5 mm in width. However, other sizes may be utilized if suitable for the purposes described herein. In an embodiment, the distal braided shaft 128 is formed by weaving together the plurality of wire members 129, 131 in opposite directions in a one-over-one pattern. The weaving pattern, number and size of the wire members 129, 131 may be varied. The wire members 129, 131 of the distal braided shaft 124 may be formed from materials such as, but not limited to, stainless steel, Nitinol, or other materials suitable for the purposes described herein. The wire members 129, 131 may also be coated prior to weaving, if desired. For example, and not by way of limitation, the wire members 129, 131 may be coated with a polymer material prior to weaving.

Although FIGS. 7-7A show details of the proximal braided shaft 124, the distal braided shaft 128 may be the same as the proximal braided shaft 124 shown in FIGS. 7-7A. It also may be similar but with some differences, such as the tightness of the weave pattern, size of the wire members, size of the perfusion openings, etc. The distal braided shaft 128 may include longitudinal stiffening wires 132, as shown in FIG. 7A. The distal braided shaft 128 may include the same or a different number of the stiffening wires 132 than the proximal braided shaft 124. In some embodiments, the distal braided shaft 128 is more flexible than the proximal braided shaft 124.

Referring to FIG. 2, a seal 121 may be provided proximal of the proximal perfusion portion 118 to prevent blood from filling the balloon catheter 100 between the inner shaft 140 and the outer shaft 110 proximal of the proximal perfusion portion 118. The seal 121 may be an O-ring with an opening for the inner shaft 140 to extend through and a body portion extending between the inner shaft 140 and the outer shaft 110. The seal 121 may be made of materials suitable for preventing blood to pass through the seal 121, such as, but not limited to, rubber, neoprene, Buna-N, Viton®, Silicone, EPDM, polyurethane, and other materials suitable for the purposes described herein.

The balloon portion 120 of the outer shaft 110 is disposed between the proximal perfusion portion 118 and the distal perfusion portion 116. In an embodiment, the lumen 134 of the balloon portion 120 acts as a perfusion lumen 136 between the distal perfusion portion 116 and the proximal perfusion portion 118. As can be seen in FIG. 2, the inner shaft 140 is disposed within the lumen 134 of the outer shaft 110. The perfusion lumen 136 is disposed between the inner shaft 140 and the outer shaft 110. The balloon portion 120 of the outer shaft 110 extends through the balloon 150 and prevents blood flow in the perfusion lumen 136 from entering the balloon 150.

The inner shaft 140 extends through the lumen 134 of the outer shaft 110 from a proximal end of the balloon catheter 100 to a distal end of the balloon catheter 100. In an embodiment, the inner shaft 140 defines a guidewire lumen 142 and an inflation lumen 144 therein, as shown in FIGS. 2-5. In other embodiments, instead of a single shaft defining both the guidewire lumen 142 and the inflation lumen 144, multiple shafts may be utilized. In the embodiment shown, the guidewire lumen 142 extends from the proximal end of the balloon catheter 100 to the distal end of the balloon catheter 100. In other embodiments, a rapid exchange configuration may be utilized wherein the guidewire lumen does not extend to the proximal end of the balloon catheter. Instead, the guidewire exits the balloon catheter 100 proximal of the balloon 150.

As can be seen in FIGS. 2-6, the inflation lumen extends from a proximal end of the balloon catheter 100 to an inflation port 146 between proximal and distal ends of the balloon 150. The inflation port 146, as best seen in FIGS. 2 and 4, extends through the balloon portion 120 of the outer shaft 110 such that inflation fluid may exit the inflation lumen 144 into an interior 151 of the balloon 150, thereby inflating the balloon 150. In the embodiment shown, there is a single inflation port 146. However, there may be multiple inflation ports 146. As can be seen in FIG. 5, the inflation port 146 extending through the perfusion lumen 136 still permits flow through the perfusion lumen 136. Additional inflation ports 146 may be added around the circumference of the inner shaft 140 while still permitting flow through the perfusion lumen 136. For example, and not by way of limitation, a second inflation port may be added 180 degrees around the circumference of the inner shaft 140 from the inflation port 146. In other embodiments, additional inflation ports may be added at different longitudinal locations along the inner shaft 140. As can be seen in FIGS. 2 and 4, the inflation lumen 144 terminates at the inflation port 146.

The inner shaft 140 may be made from materials such as, but not limited to, polymeric materials, non-exhaustive examples of which include polyethylene, polyether block amide (PEBA), polyamide and/or combinations thereof, either blended or co-extruded.

The distal tip 114 is disposed at the distal end of the balloon catheter 100. The distal tip 114 is configured to provide a soft distal end to the balloon catheter 100 such that the distal tip 114 does not damage the surrounding tissue as the balloon catheter 100 is advanced through the vasculature of the patient. The distal tip 114 may be formed from materials such as, but not limited to, polymers, or other materials suitable for the purposes described herein. The distal tip 114 may be coupled to the distal braided shaft 128 in a manner such as, but not limited to adhesives, fusing, welding, or other methods suitable for the purposes disclosed herein. Further, the inner shaft 140 may be coupled to the distal tip 114 in a manner such as, but not limited to adhesives, fusing, welding, or other methods suitable for the purposes disclosed herein.

The balloon 150 includes a proximal neck 152 coupled to the balloon portion 120 of the outer shaft 110 at a proximal bond 154, and a distal neck 156 coupled to the balloon portion 120 of the outer shaft 110 at a distal bond 158. The proximal bond 154 and the distal bond 158 may be a weld, adhesive, or other mechanical connection. The balloon 150 can be any appropriate shape or size, and any material which is relatively elastic and deformable. Non-exhaustive examples of materials for the balloon 150 include polymers such as polyethylene, polyether block amide (PEBA) e.g. PEBAX, polyethylene terephthalate (PET), nylon, polyurethane.

The hub or luer 160 is disposed proximal of the balloon catheter 100 and remains outside of the patient. The luer 160 includes lumens communicating with the guidewire lumen 142 and the inflation lumen 144. Thus, a guidewire may extend through the guidewire lumen 142 and through a corresponding lumen in the luer 160. An inflation fluid, such as saline, may be injected into a lumen in the luer 160 which is in fluid communication with the inflation lumen 144 when it is desired to inflate the balloon 150.

With the above construction in mind, and as can be seen in FIGS. 1-6, blood may flow into the perfusion lumen 136 through the distal perfusion openings 130 of the distal perfusion portion 116, through the perfusion lumen 136, and out of the proximal perfusion openings 127 of the proximal perfusion portion 118. Blood flow may be in the opposite direction (i.e., entering the proximal perfusion openings 127 and exiting the distal perfusion openings 130) depending on the location where the balloon catheter 100 is used and the orientation of the balloon catheter 100. For example, for use in the aortic valve, if the balloon catheter 100 is advanced from the aorta through the aortic valve, blood flow will be from the distal end of the balloon catheter 100 towards the proximal end of the balloon catheter 100, as shown in FIG. 1 and FIGS. 8-11. Thus, blood will flow into the distal perfusion openings 130 and out of the proximal perfusion openings 127. However, if the balloon catheter 100 is advanced transapically from the left ventricle through the aortic valve, blood will flow into the proximal perfusion openings 127 and out of the distal perfusion openings 130.

Figure 11:
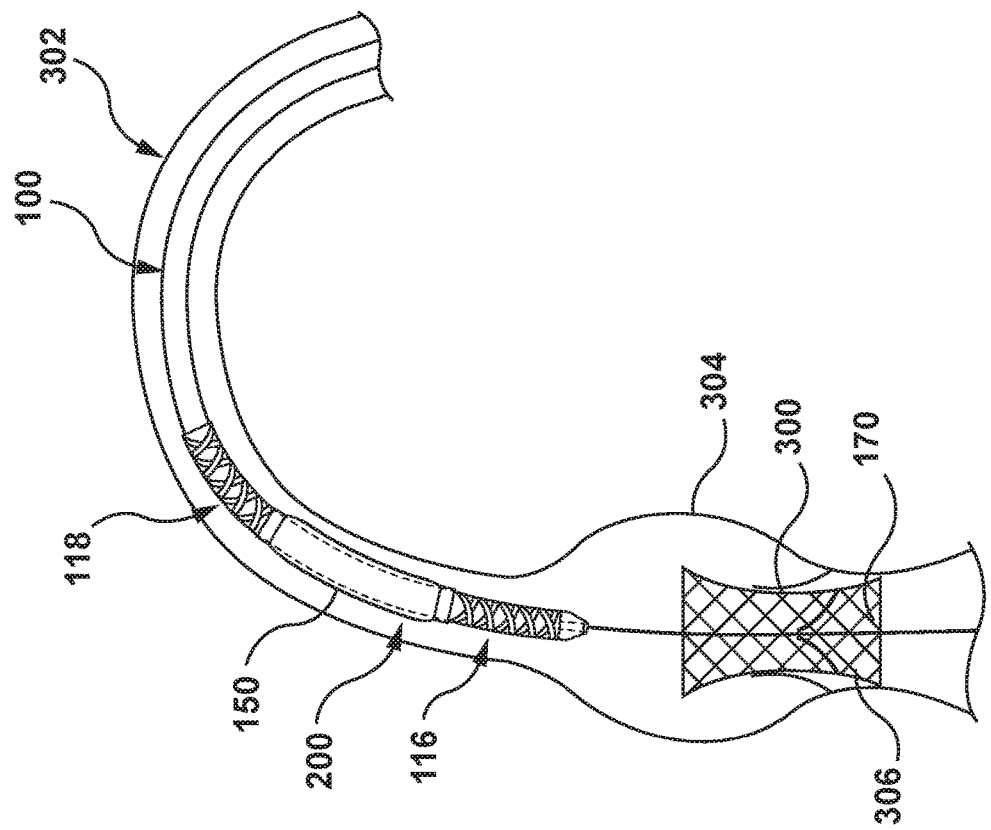

FIGS. 8-11 illustrate schematically a method of delivering and deploying a prosthetic heart valve 200 at the site of a native aortic valve 300 using the balloon catheter 100. The prosthetic heart valve 200 may be any balloon-expandable prosthetic heart valve. Generally, the prosthetic heart valve 200 includes a frame 202 and a valve prosthesis 204 coupled to an interior portion of the frame (FIG. 11). The prosthetic heart valve 200 is radially compressed or crimped onto the balloon 150 of the balloon catheter 100. Although the method of FIGS. 8-11 illustrate delivery and deployment of a prosthetic heart valve using the balloon catheter 100, this is not meant to be limiting. In other embodiments, the balloon catheter 100 can be used in other procedures, such as, but not limited to, a valvuloplasty procedure. Using the balloon catheter 100 in a valvuloplasty procedure is similar to the method described with respect to FIGS. 8-11 except that a prosthetic heart valve is not disposed over the balloon 150 of the balloon catheter.

Figure 8:
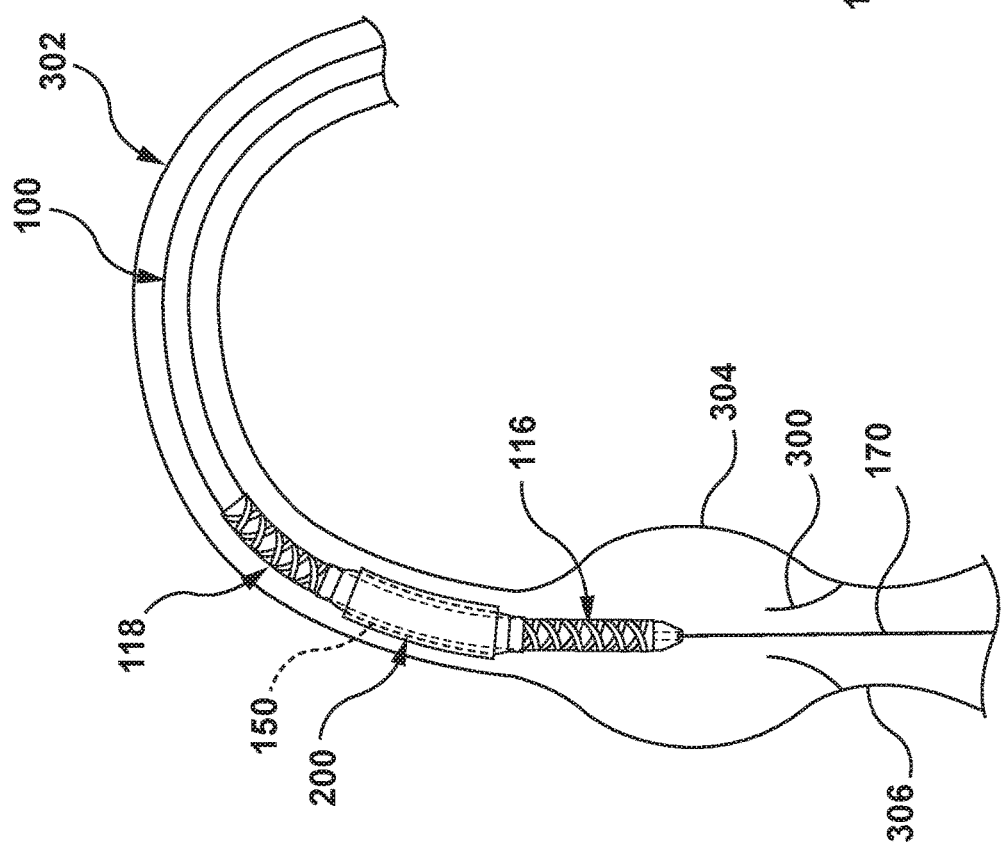

As shown schematically in FIG. 8, the balloon catheter 100 is advanced through the patient's vasculature to the site of a native aortic valve 300. In an embodiment, the balloon catheter is advanced over a guidewire 170. In the embodiment of FIGS. 8-11, the balloon catheter 100 is advanced transluminally through the lumen of the aorta 302. The balloon catheter 100 accesses the vasculature and is advanced using established percutaneous transcatheter procedures.

Figure 9:
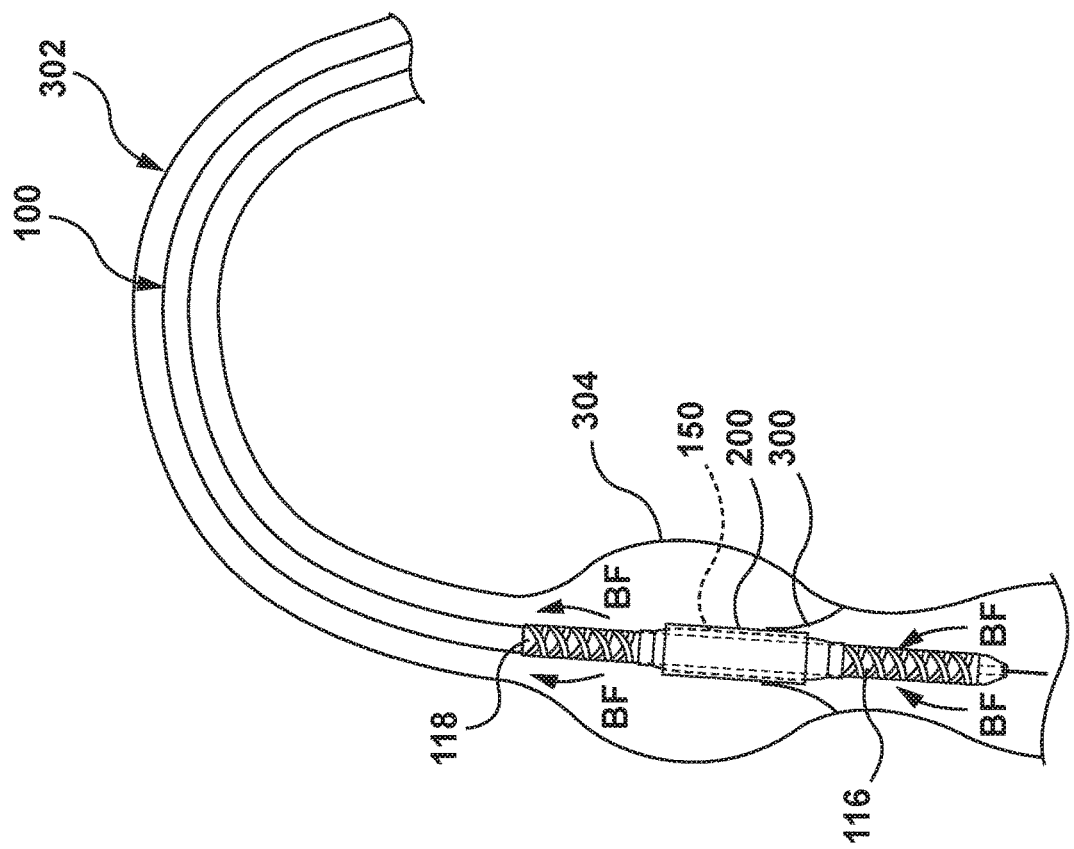
FIGS. 8-11 are schematic illustrations of a method of delivering and deploying a balloon-expandable prosthetic heart valve using the balloon catheter of FIG. 1.

The balloon catheter 100 is then advanced between the native leaflets of the native aortic valve 300 such that the prosthetic heart valve 200 is disposed between the native leaflets, as shown in FIG. 9. The distal perfusion portion 116 is disposed upstream of the native leaflets of the native aortic valve 300, and the proximal perfusion portion 118 is disposed downstream of the native leaflets of the native aortic valve 300. At this juncture, if there is any blockage of blood flow through the native aortic valve 300, blood may flow into the distal perfusion openings 130, within the perfusion lumen 136, and out of the proximal perfusion openings 127, as indicated by the arrows BF in FIG. 9.

Figure 10:
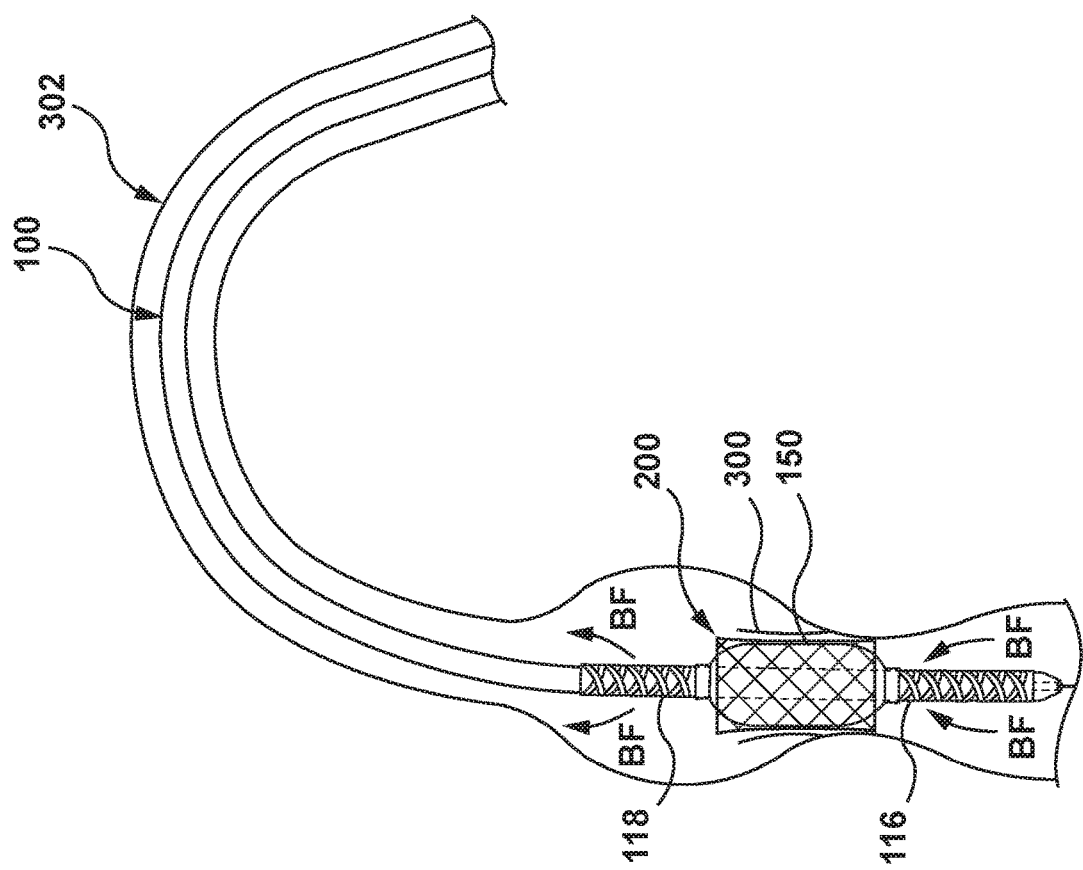

With the balloon catheter 100 located such that the prosthetic heart valve 200 will be deployed at the desired location, an inflation fluid is injected into the inflation lumen 144. The inflation fluid exits the inflation lumen 144 through the inflation port 146 and into the interior 151 of the balloon 150, thereby inflating the balloon 150. Inflation of the balloon 150 radially expands the balloon 150, thereby radially expanding the prosthetic heart valve 200 mounted thereon, as shown in FIG. 10. With the balloon 150 inflated, blood cannot flow through the native aortic valve 300 from the annulus 306 side of the aortic valve to the sinus 304 side of the aortic valve 300 around the balloon 150. As described in the Background section above, if measures are not taken, blood from the left ventricle pushes against the balloon and may cause the balloon to move (or watermelon seed), which results in movement of the heart valve prosthesis 200. This may result in inaccurate placement of the heart valve prosthesis 200, which may lead to further complications such a paravalvular leakage. However, using the balloon catheter 100, blood may flow into the distal perfusion openings 130, within the perfusion lumen 136, and out of the proximal perfusion openings 127, as indicated by the arrows BF in FIG. 10. This prevents a build-up of pressure against the balloon 150 by blood attempting to be pushed through the native aortic valve 300.

Once the heart valve prosthesis 200 has been radially expanded and is in place at the native aortic valve 300, the inflation fluid may be drained from the inflation lumen 144 and the balloon 150, thereby deflating the balloon 150. The balloon catheter 100 may be retracted from the site of the native aortic valve 300, as shown in FIG. 11, thereby leaving the prosthetic heart valve 200 in place.

FIGS. 8-11 describe a transluminal advancement of the balloon catheter through the aorta to the site of the native aortic valve. However, this is merely an example of one type of procedure. The balloon catheter 100 and the general method described above may be used for other heart valves, such as the mitral or tricuspid valves, and using other access points. For example, and not by way of limitation, the balloon catheter 100 and heart valve prosthesis may be delivered via a transfemoral, transapical, transseptal, transatrial, transventrical, or transaortic procedure. In a specific example, and not by way of limitation, the balloon catheter 100 may be advanced transapically through the apex of the heart and advanced through the left ventricle to either the aortic valve or the mitral valve. Depending on the orientation of the balloon catheter and the native heart valve to with the balloon catheter 100 is advanced, blood may flow into the distal perfusion portion and out of the proximal perfusion portion or into the proximal perfusion portion and out of the distal perfusion portion. Further, as described above, the balloon catheter 100 and the general method described above may be used in other procedures, such a valvuloplasty procedures, without a prosthetic heart valve disposed on the balloon 150 of the balloon catheter 100.

While only some embodiments have been described herein, it should be understood that it has been presented by way of illustration and example only, and not limitation. Various changes in form and detail can be made therein without departing from the spirit and scope of the invention, and each feature of the embodiments discussed herein, and of each reference cited herein, can be used in combination with the features of any other embodiment. All patents and publications discussed herein are incorporated by reference herein in their entirety.

What is claimed is:

1. A method comprising:
   transluminally advancing a balloon catheter through a patient's vasculature to a treatment site, the balloon catheter including a balloon coupled to an outer shaft; and
   expanding the balloon of the balloon catheter at the treatment site, wherein with the balloon expanded, blood flow from an upstream side of the balloon flows into upstream perfusion openings in the outer shaft on the upstream side of the balloon, through a perfusion lumen within the outer shaft, and out of downstream perfusion openings in the outer shaft on a downstream side of the balloon, wherein the blood flow out of the downstream perfusion openings is through openings between downstream wire members woven together to form a downstream braided shaft, and wherein the blood flow into the upstream perfusion openings is through openings between upstream wire members woven together to form an upstream braided shaft.

2. The method of claim 1, wherein the downstream perfusion openings are each between 0.1 mm and 5 mm in width to enable blood flow therethrough.

3. The method of claim 2, wherein the upstream perfusion openings are each between 0.1 mm and 5 mm in width to enable blood flow therethrough.

4. The method of 1, wherein balloon catheter further includes an inner shaft disposed within the outer shaft such that the perfusion lumen is disposed between an inner surface of the outer shaft and an outer surface of the inner shaft such that blood flows between the inner shaft and the outer shaft from the upstream side of the balloon to the downstream side of the balloon.

5. A method comprising:
   transluminally advancing a balloon catheter through a patient's vasculature to a location of a native heart valve, the balloon catheter including a balloon coupled to an outer shaft and a heart valve prosthesis mounted on the balloon; and expanding the balloon of the balloon catheter at the native heart valve to radially expand the heart valve prosthesis, wherein with the balloon expanded, blood flow from an upstream side of the balloon flows into upstream perfusion openings in the outer shaft on the upstream side of the balloon, through a perfusion lumen within the outer shaft, and out of downstream perfusion openings in the outer shaft on a downstream side of the balloon, wherein the blood flow out of the downstream perfusion openings is through openings between downstream wire members woven together to form a downstream braided shaft, and wherein the blood flow into the upstream perfusion openings is through openings between upstream wire members woven together to form an upstream braided shaft.

6. The method of claim 5, wherein the downstream perfusion openings are each between 0.1 mm and 5 mm in width to enable blood flow therethrough.

7. The method of claim 6, wherein the upstream perfusion openings are each between 0.1 mm and 5 mm in width to enable blood flow therethrough.

8. The method of claim 5, wherein transluminally advancing the balloon catheter through the patient's vasculature comprises advancing the balloon catheter to a native aortic valve.

9. The method of claim 5, wherein transluminally advancing the balloon catheter through the patient's vasculature comprises advancing the balloon catheter to a native mitral valve.

10. A method of making a balloon catheter comprising:
    attaching a balloon to an outer shaft, wherein the outer shaft includes proximal perfusion openings proximal of a proximal end of the balloon and distal perfusion openings distal of the balloon, wherein the proximal perfusion openings and the distal perfusion openings are formed by weaving together a plurality of wire members such that the proximal perfusion openings and the distal perfusion openings are formed between the adjacent woven wire members, wherein the proximal perfusion openings and the distal perfusion openings are sized to permit blood flow therethrough such that blood flows into the proximal perfusion openings upstream of the balloon, through a perfusion lumen within the outer shaft, and out of the distal perfusion openings downstream of the balloon.

11. The method of claim 10, further comprising inserting an inner shaft within the outer shaft to form the perfusion lumen between an outer surface of the inner shaft and an inner surface of the outer shaft such that blood flow enters the perfusion lumen through the proximal perfusion openings and exits the perfusion lumen through the distal perfusion openings.

12. The method of claim 10, wherein the wire members are woven to form the proximal openings and the distal perfusion openings of 0.1 mm to 5 mm in width.

13. The method of claim 10, wherein the wire members are woven in a one-over-one pattern.

14. The method of claim 10, wherein the wire members are coated prior to weaving the wire members to form the proximal perfusion openings and the distal perfusion openings.

15. The method of claim 10, further comprising attaching at least one longitudinal stiffening wire to the outer shaft proximal of the balloon to provide pushability to the outer shaft.

16. The method of claim 15, wherein attaching at least one stiffening wire comprises attaching a plurality of stiffening wires spaced apart around an inner circumference of the outer shaft.

\* \* \* \* \*